(12) United States Patent
Wurzbach et al.

(10) Patent No.: US 8,549,930 B2
(45) Date of Patent: Oct. 8, 2013

(54) METHOD OF EVALUATING GREASE AND EXTRUSION DIE FOR THE METHOD

(76) Inventors: Richard N. Wurzbach, Brogue, PA (US); Andreas Retzlaff, Glen Rock, PA (US)

(*) Notice: Subject to any disclaimer, the term of this patent is extended or adjusted under 35 U.S.C. 154(b) by 100 days.

(21) Appl. No.: 13/320,565

(22) PCT Filed: May 15, 2009

(86) PCT No.: PCT/US2009/044091
§ 371 (c)(1),
(2), (4) Date: Nov. 15, 2011

(87) PCT Pub. No.: WO2009/140571
PCT Pub. Date: Nov. 19, 2009

(65) Prior Publication Data
US 2012/0055266 A1 Mar. 8, 2012

Related U.S. Application Data

(60) Provisional application No. 61/053,856, filed on May 16, 2008.

(51) Int. Cl.
*G01F 1/37* (2006.01)
(52) U.S. Cl.
USPC ....................................... 73/861.52

(58) Field of Classification Search
USPC ............................ 73/861.52, 864.73
See application file for complete search history.

(56) References Cited

U.S. PATENT DOCUMENTS

| | | | |
|---|---|---|---|
| 4,030,328 A | 6/1977 | Wagner | |
| 4,197,069 A | 4/1980 | Cloeren | |
| 4,468,366 A | 8/1984 | Socha, Jr. et al. | |
| 5,392,632 A * | 2/1995 | Umeda et al. | 73/1.73 |
| 6,471,215 B1 * | 10/2002 | Drago et al. | 277/412 |
| 7,984,661 B2 * | 7/2011 | Wurzbach | 73/864.73 |

FOREIGN PATENT DOCUMENTS

WO 2004045827 A1 6/2004

OTHER PUBLICATIONS

International Search Report in corresponding PCT application PCT/US09/044091 dated Dec. 30, 2009.

* cited by examiner

*Primary Examiner* — Jewel V Thompson
(74) *Attorney, Agent, or Firm* — Hooker & Habib, P.C.

(57) ABSTRACT

A method of measuring a characteristic property of grease includes pushing a constant volumetric flow of grease through an extrusion die and measuring the force needed to extrude the grease from the die. The die includes a flow restriction that increases the force required to flow the grease.

15 Claims, 8 Drawing Sheets

METHOD OF EVALUATING GREASE AND EXTRUSION DIE FOR THE METHOD

FIELD OF THE DISCLOSURE

The disclosure relates to a method of evaluating grease, and an extrusion die for the method.

BACKGROUND OF THE DISCLOSURE

It is estimated that 90% of all machine bearings are lubricated by grease. While oil analysis is a widespread tool for monitoring bearing and lubricated component health of important oil lubricated equipment, grease analysis is not generally adopted in a similar manner for important grease lubricated machines. Analyzing a sample of grease taken from a grease-lubricated bearing is sometimes performed to determine whether the grease has reached the end of its usable life and should be replaced. The ability to adopt regular and routine grease analysis for important grease lubricated machines, however, has been historically limited by the inability to obtain representative samples of the grease and by the complexity of the grease analysis itself.

Pending U.S. patent application Ser. No. 12/107,873 filed by one of the co-applicants herein discloses improved grease sampling devices used to obtain representative samples of grease. This application discloses a method of measuring a quantitative measure of a characteristic material property of grease that can be more easily used to determine the consistency, and thus the health, of used grease.

One known method of measuring a material property of grease is the cone penetration test, ASTM D217. A grease sample is heated and placed below a test cone. The cone drops into the heated grease and the depth of cone penetration is a measure of grease consistency. The cone penetration test requires a large volume sample and is not normally performed on samples of used grease.

Another method of evaluating the consistency of grease is Thermal Gravimetric Analysis (TGA). TGA measures the loss of volatile compounds in a grease sample with increasing temperature. The test is performed in a controlled nitrogen or oxygen atmosphere and requires relatively expensive test equipment.

Thus there is a need for a method of evaluating the consistency of grease that overcomes the problems of the known test methods.

SUMMARY OF THE DISCLOSURE

Disclosed is a method of measuring a characteristic property of grease that is related to the consistency of the grease. The method does not require a large grease sample and can be conducted using inexpensive equipment.

The disclosed method preferably involves measuring the force needed to extrude a constant flow of grease through a discharge opening that defines the cross-sectional shape of the extruded grease. The average force to extrude the grease provides a measurement related to the consistency of the grease. The measurement is useful in evaluating the health of used grease, that is, in deciding whether the grease of a grease-lubricated component should be replaced.

In a preferred embodiment of the method, the grease is pushed through an extrusion die having an inlet opening and a flow restriction downstream from the inlet opening. The flow restriction increases the average force required to push the grease through the die. The increased force makes the measured average force less susceptible to force variations caused by inhomogenieties or contaminants within the grease being flowed through the die, thereby reducing data scatter and providing more dependable test results.

In preferred embodiments of the die, the grease flows past a baffle that obstructs contaminants in the grease. The baffle preferably extends at an acute angle with respect to the downstream direction of flow so that the contaminants are directed towards the downstream end of the baffle and provide less of an obstruction to flow.

In yet other preferred embodiments of the die, the grease flows through a relatively large-volume chamber located between the flow restriction and the discharge opening. The chamber fills up with grease to discharge a uniform flow of grease to the discharge opening.

The method of evaluating grease can be performed using relatively inexpensive equipment. A piston pushes the grease sample through the die. The piston is driven at a constant speed by an electric motor. A load cell placed between the piston and the motor measures the force applied to the piston. A graph of the force applied to the piston versus time enables the average force to be easily determined.

The equipment is preferably housed in an environmental chamber that warms the grease to a standard temperature before testing, and maintains the other components that contact the grease at that temperature.

The test equipment and extrusion die used for performing the evaluation method can be easily adapted to flow grease held in the grease sampling device disclosed in U.S. patent application Ser. No. 12/107,873, which pending patent application is incorporated herein by reference as if fully set forth here. The extrusion die is threaded onto one end of the device, and the motor drives the piston used in the grease sampling device to discharge the grease sample from the grease sampling device and push the grease through the extrusion die. It is not necessary to transfer the grease sample from the grease sampling device to another container when performing the test.

Other objects and features will become apparent as the description proceeds, especially when taken in conjunction with the accompanying drawing sheets illustrating two testing machines and two extrusion dies.

DESCRIPTION OF THE PREFERRED EMBODIMENTS

The disclosed method preferably involves measuring the force needed to extrude a constant flow of grease through a discharge opening that defines the cross-sectional shape of the extruded grease. The average force to extrude the grease provides a measurement related to the consistency of the grease. The measurement is useful in evaluating the health of used grease, that is, in deciding whether the grease of a grease-lubricated component should be replaced.

Figure 1:
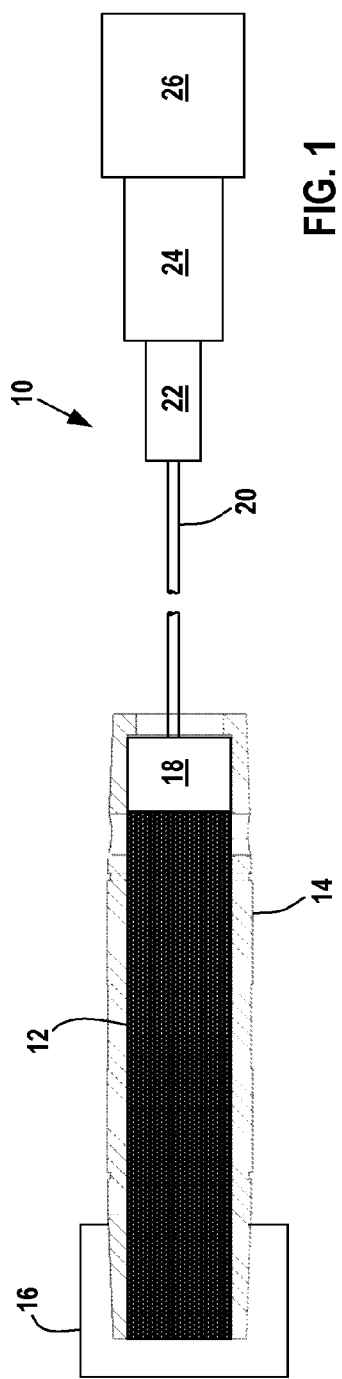
FIG. 1 is a schematic illustration of a first embodiment testing machine flowing a sample of used grease through a first embodiment extrusion die.

FIG. 1 illustrates a testing machine 10 for extruding a grease sample 12 contained within a housing 14 through an extrusion die formed as a piston cap 16 and attached to an open end of the housing 14. The grease sample 12 preferably has a mass of between about one gram and one and one-half grams. Housing 14, piston 18 within the housing 14, and the piston rod 20 extending from the piston 18 form part of a grease sampling device that is disclosed in U.S. patent application Ser. No. 12/107,873. Testing machine 10 has a load cell 22 that is placed between the free end of the piston rod 20 and a drive arm 24. Drive arm 24 is driven axially at a predetermined speed by an electric motor 26, driving the piston 18 axially toward the piston cap 16 at a constant speed and thereby extruding grease through the piston cap 16 at a predetermined flow rate.

The extruded grease flows onto a glass substrate (not shown) that preferably moves away from the piston cap 16 at a speed substantially greater than the speed of the grease flowing out of the piston cap 16, thereby flowing a smooth ribbon of grease onto the substrate without impeding the flow of the grease.

Load cell 22 measures the force applied by the drive arm 24 on the piston rod 20 as the piston 18 moves towards the piston cap 16. This measurement provides a quantitative measure of a characteristic material property of the grease.

Figure 2:
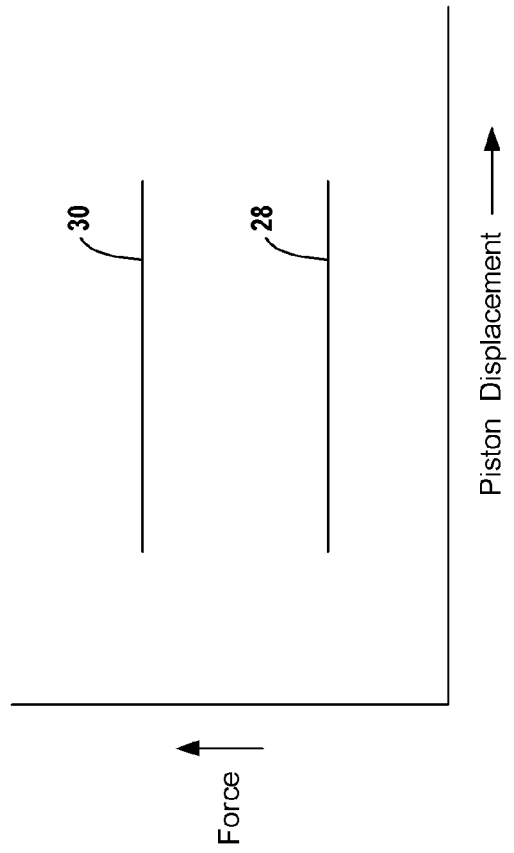
FIG. 2 is a chart of force as a function of piston displacement for two grease samples, each sample flowed through the extrusion die and using the testing machine shown in FIG. 1.
Figure 3:
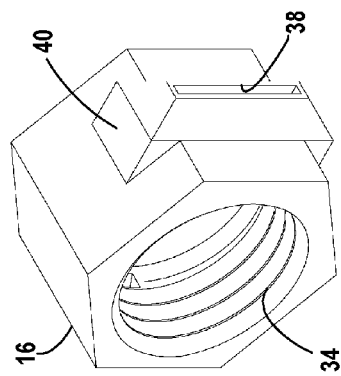
FIG. 3 is a perspective view of the extrusion die shown in FIG. 1.
Figure 4:
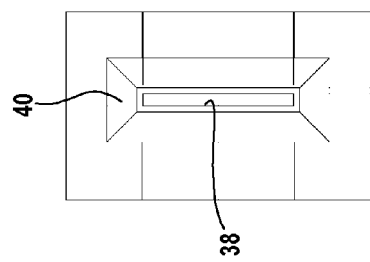
FIG. 4 is a side view of the extrusion die shown in FIG. 1.
Figure 5:
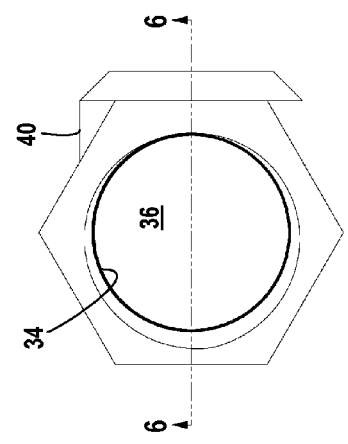
FIG. 5 is an end view of the extrusion die shown in FIG. 1.
Figure 6:
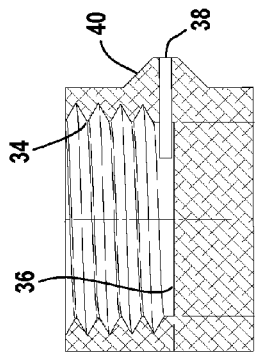
FIG. 6 is a vertical sectional view of the extrusion die shown in FIG. 1 and taken along line 6-6 of FIG. 5.

FIG. 2 illustrates two force curves 28, 30 measured on a fresh, unused sample of a grease used in a grease-lubricated component and a representative sample of the used grease from that grease-lubricated component respectively. Both samples were extruded through the piston cap 16 at the same flow rate and at the same temperature. As can be seen in FIG. 2, the average force required to extrude the used grease is substantially lower than the average force required to extrude the fresh grease. This indicates that the used grease should be replaced in the component.

For other types of greases the average force to extrude used grease may be higher than the average force to extrude fresh grease.

FIGS. 3-6 illustrate the piston cap 16. Piston cap 16 is a cylindrical cap having a blind threaded bore 34 opening from one end of the cap and a wall 36 closing the opposite end of the cap. A metering orifice or extrusion discharge opening 38 is formed in a radial extension body 40 extending from one side of the cap. Orifice 38 has a rectangular cross section and extends from the outside of the cap and opens into the bore 34 adjacent the wall 36. In the illustrated embodiment the orifice 38 has a rectangular cross section, with sides of 0.020 inches by 0.250 inches.

Threaded bore 34 is sized to threadingly engage the open end of the housing 14. Grease extruded through the orifice 38 during the performance of the flow test flows out of the orifice as a rectangular ribbon of extruded grease flowing at a right angle to the movement of the piston 18.

Figure 7:
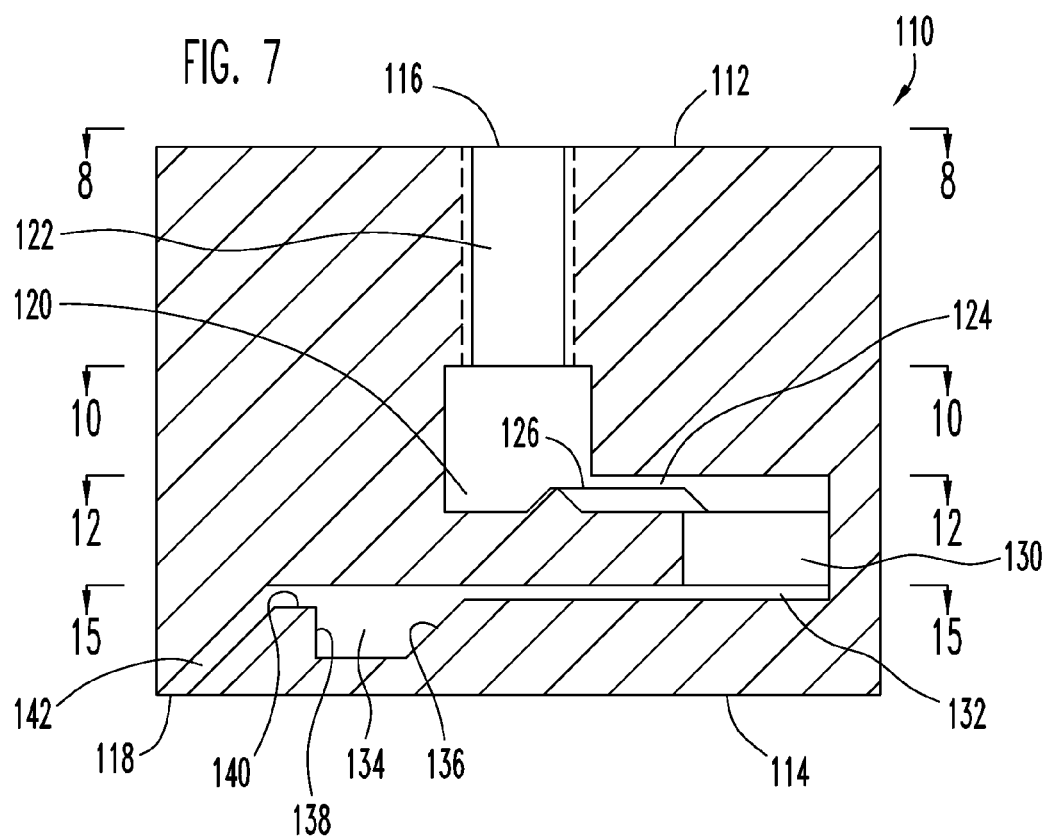
FIG. 7 is a vertical sectional view of a second embodiment extrusion die.

FIG. 7 illustrates a second embodiment extrusion die 110. Extrusion die 110 is generally cube-shaped, with spaced apart, generally planar end faces 112, 114. An inlet opening 116 is formed on the upper end face 112 and a discharge opening 118 is formed on the lower end face 114. The shape of the discharge opening 118 defines the shape of the grease extruded from the die. In the illustrated embodiment the discharge opening 118 is rectangularly shaped and is 0.5 inches wide by 0.03 inches high.

A flow channel 120 flows grease from the inlet opening 116 to the discharge opening 118 in the downstream direction of the channel. The flow channel 120 includes a circular inlet channel 122 that is 0.2 inches in diameter and extends about 0.45 inches inwardly perpendicular to the die face 112 from the inlet opening 116, and a first restricted flow channel portion 124 that extends parallel to the die face 112 from the inlet channel 122. The upper 0.3 inches of the flow channel 120 from the inlet opening 116 is threaded to receive the open end of a housing 14.

The restricted flow channel 124 has a rectangular cross-sectional flow area that is 0.250 inches wide and 0.050 inches high. Flow channel 124 has substantially less flow area than does the inlet channel 122, and so presents a flow restriction to the grease flowing from the inlet channel 122. The reduced flow area increases the force necessary to flow grease through the flow channel 120 to the discharge opening, reducing data scatter.

Disposed within the restricted flow channel 124 is a baffle 126. Baffle 126 provides a mechanical barrier or obstruction to the flow of grease through the flow portion 124 that helps resist clogging of the flow channel 120 caused by dirt or other particulate contaminants found in used grease. The baffle 126 preferably is not perpendicular to the flow channel 124 but instead extends at an oblique angle with respect to the flow channel 124, or in other words, the downstream end of the baffle 126 is spaced substantially downstream from the upstream end of the baffle 126.

Figure 12:
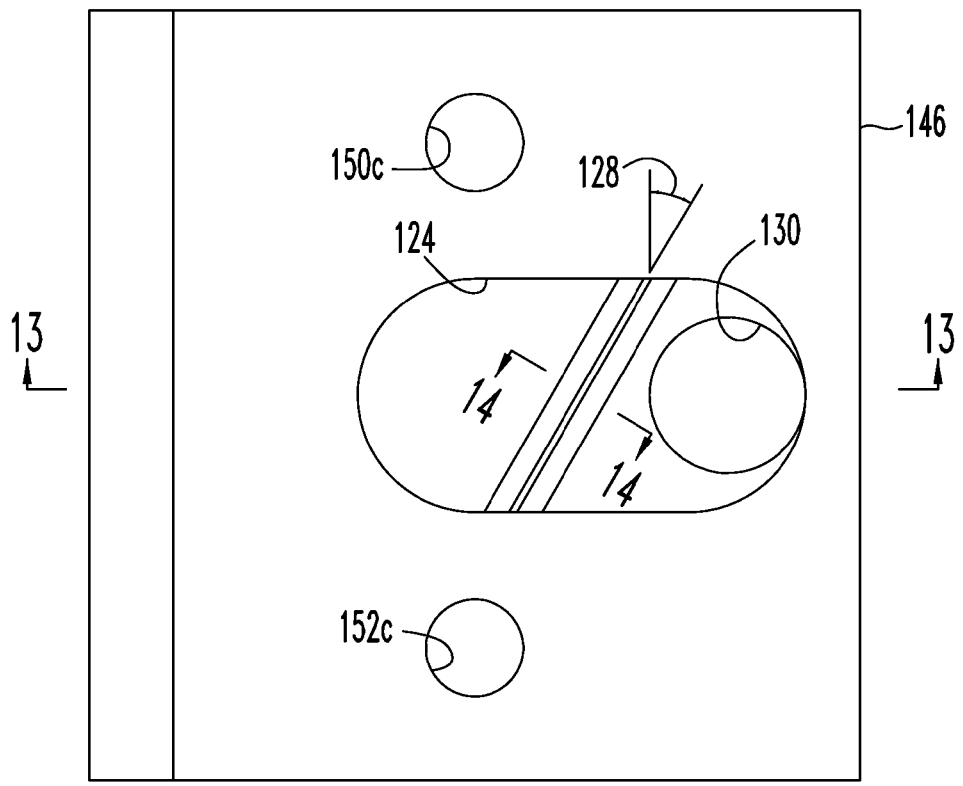
FIG. 12 is a top view of the lower intermediate component block of the extrusion die shown in FIG. 7 and taken along line 12-12 of FIG. 7.
Figure 13:
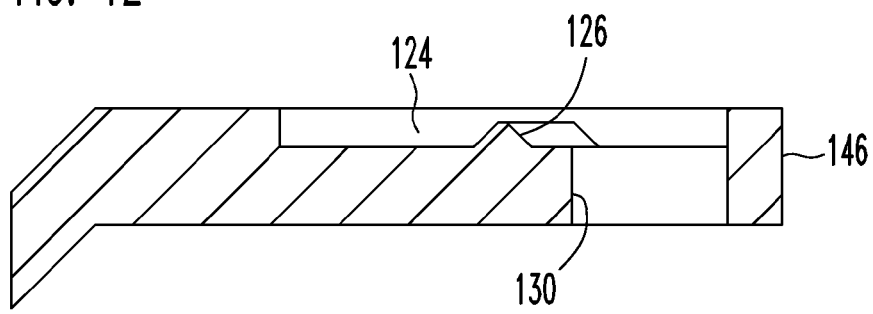
FIG. 13 is a sectional view of the lower intermediate component block taken along line 13-13 of FIG. 12.
Figure 14:
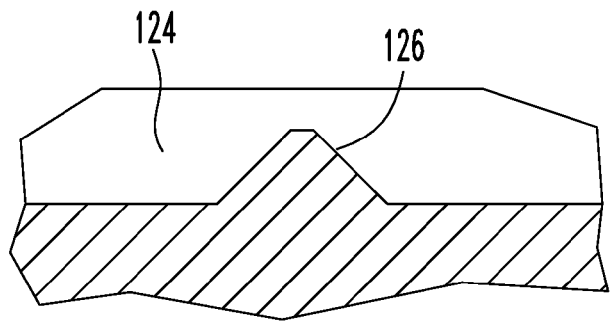
FIG. 14 is a partial sectional view of the lower intermediate component block and taken along line 14-14 of FIG. 12.
Figure 15:
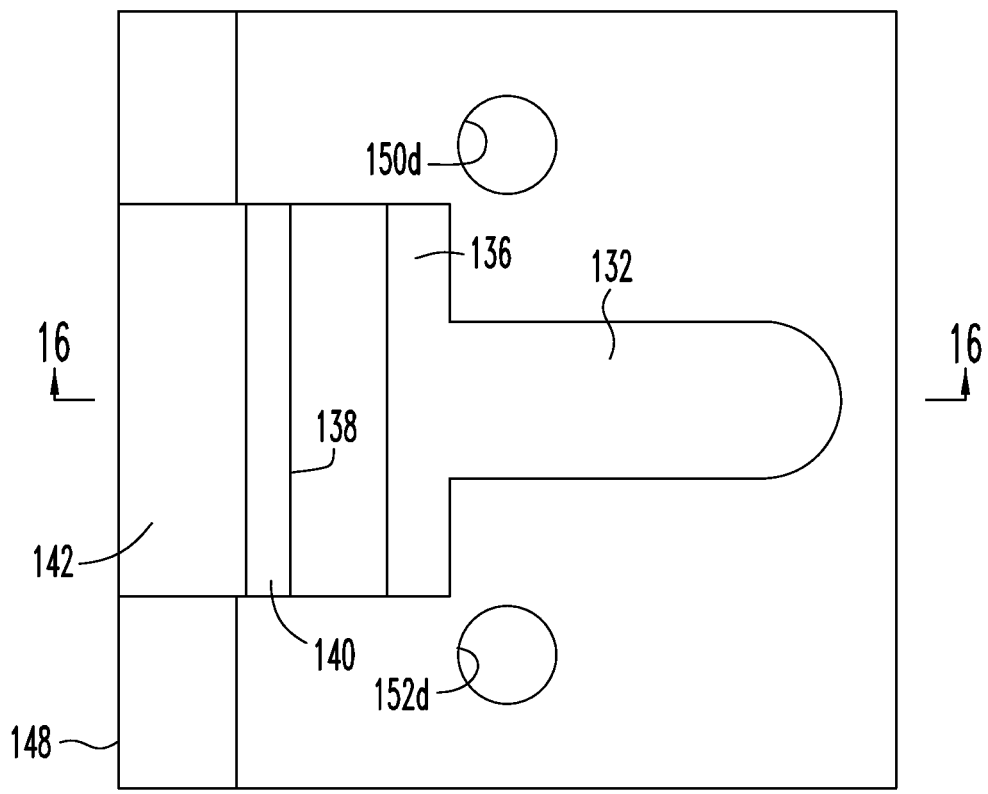
FIG. 15 is a top view of the bottom component block of the extrusion die shown in FIG. 7 and taken along lines 15-15 of FIG. 7.
Figure 16:
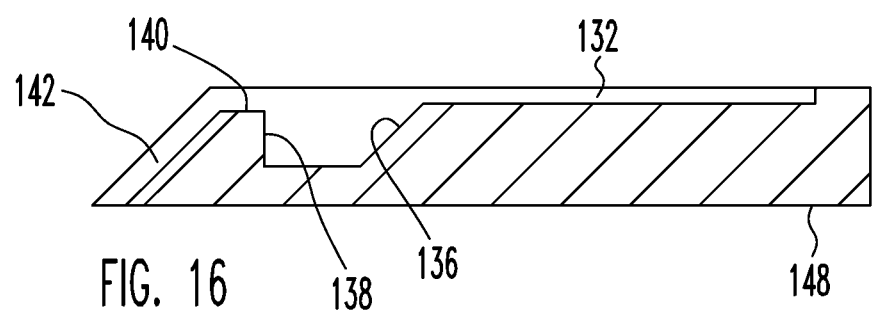
FIG. 16 is a sectional view of the bottom component block taken along line 16-16 of FIG. 15.

In the illustrated embodiment the baffle 126 is oriented at an angle 128 of 30 degrees with respect to the flow channel 124 (see FIG. 12), and is formed as a generally "V" shaped wall that extends from one side of the flow channel 124 partway into the flow path (see also FIGS. 12-14). The top of the baffle 126 is spaced about 0.0175 inches from the top of the upper wall of the flow channel 124, further restricting the flow of grease through the flow channel 120. The flow of grease against the angled baffle 126 urges dirt and contaminants held back by the baffle 126 toward the downstream end of the baffle, reducing the likelihood of clogging.

In other embodiments the baffle 126 could block the entire flow path and have multiple openings extending through the wall thickness that permits the flow of grease while blocking contaminants.

The first restricted flow channel 124 discharges into a circular flow passage 130 located downstream from the baffle 126. Flow passage 130 extends perpendicularly to the die face 112 a distance of about 0.150 inches, and flows away from the die face 122 from the flow channel 124 to a second restricted flow channel 132. Flow passage 130 has a diameter equal to the diameter of the inlet flow passage 124.

Second restricted flow channel 132 has a rectangular flow area that is the same 0.250-inch width as the restricted flow channel 124 but is only 0.02 inches high. Flow channel 132 extends parallel with the die face 112 a distance of about 0.525 inches and discharges into an optional enlarged chamber or reservoir 134.

Reservoir 134 has a width equal to the width of the discharge opening 118 and has a maximum cross sectional area that is 0.5 inches wide by 0.1 inches high. The reservoir 134 has a sloped wall 136 that extends downwardly from the flow channel 132 to the bottom of the reservoir 134, and a downstream wall or weir 138 spaced about 0.3 inches from the end of the flow channel 132. Weir 138 has a horizontal upper wall 140 spaced 0.03 inches from the upper side of the flow channel 120 that extends about 0.063 inches in the downstream direction.

Reservoir 134 discharges into a flow channel 142 that flows to the discharge opening 118. Flow channel 142 extends about 0.2 inches from the reservoir 134 to the discharge opening 118, and extends away from the die face 112 at an angle of 45 degrees. Flow channel 142 has a cross sectional flow area the same dimensions as is the discharge opening 118.

In performing a test using the testing machine 10, a housing 12 filled with a grease sample is threaded to the extrusion die 110. The testing machine 12 drives the piston 18 to force grease through the flow channel 120. The grease makes a right-angled turn from the inlet channel 122 to the flow restriction 124, and flows past the baffle 126. The baffle 126 helps trap contaminants behind the baffle wall as previously described. The contaminants may cause transient spikes in the force applied to the piston 18 during the flow of the grease, providing additional data points that may be helpful in evaluating the health of the grease.

The grease then makes two right-angle turns from the first flow restriction 124 entering and leaving the flow channel 130 and entering the second flow restriction 132. The grease flows through the second flow restriction 132 in the opposite direction from the flow through the first flow restriction 124. The grease then flows along the flow channel 130 and flows into the reservoir 134. The flow of grease will initially fill the reservoir 134 before overflowing the weir 136 and entering the flow channel 142. The reservoir 134 enables the cross sectional area of the grease flow to increase from that of the flow restriction 132 to that of the flow channel 142 with uniform flow through the flow channel 142 and without gaps or voids in the grease extruding from the discharge outlet 118. The reservoir 134 can be eliminated in possible embodiments if the type of grease being tested discharges uniformly from the discharge outlet 1118 without such a reservoir 134.

The illustrated die block 110 is intended for one-time use and is formed from four separate injection-molded block components 144, 145, 146, and 148 as shown in FIGS. 8-16. Top block component 144 includes upper die face 112 and the threaded portion of inlet flow channel 142. Upper intermediate block component 147 includes the unthreaded lower portion of the inlet flow channel 142. Lower intermediate component 148 includes the flow channel 124, baffle 126, and flow channel 130. The bottom component 148 includes lower die face 114, the second flow restriction 132, reservoir 134, flow channel 144, and discharge opening 118. The blocks are glued together to form an extrusion die 110, with a pair of alignment holes 150, 152 extending through each component block to align the blocks for assembly.

Figure 17:
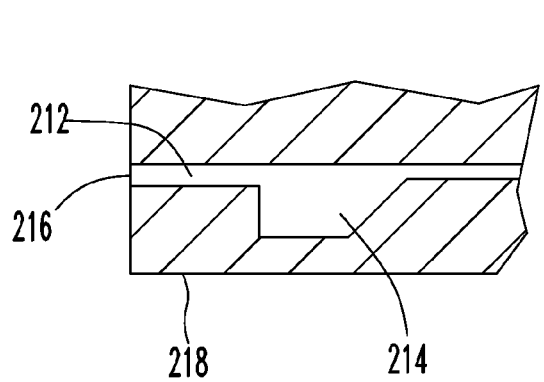
FIG. 17 is a partial vertical sectional view of a third embodiment extrusion die.
Figure 8:
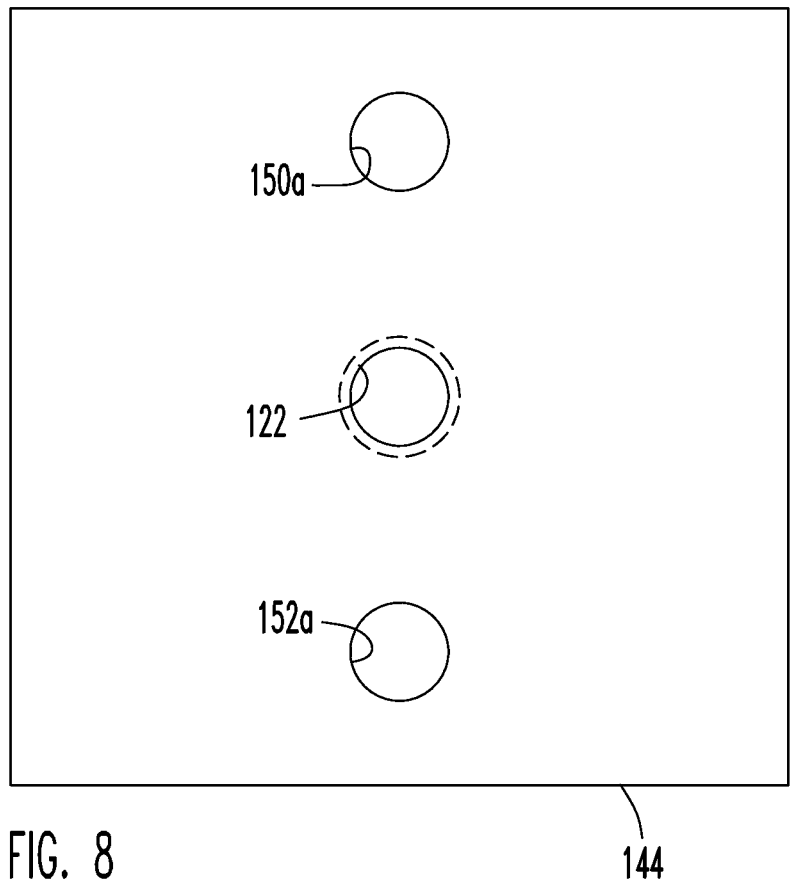
FIG. 8 is a top view of the top component block of the extrusion die shown in FIG. 7 and taken along line 8-8 of FIG. 7.
Figure 9:
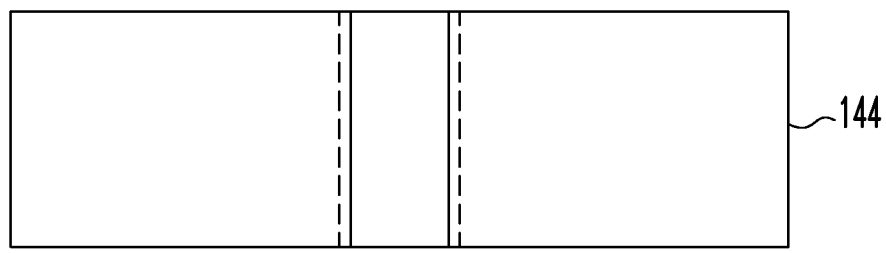
FIG. 9 is a side view of the upper component block.
Figure 10:
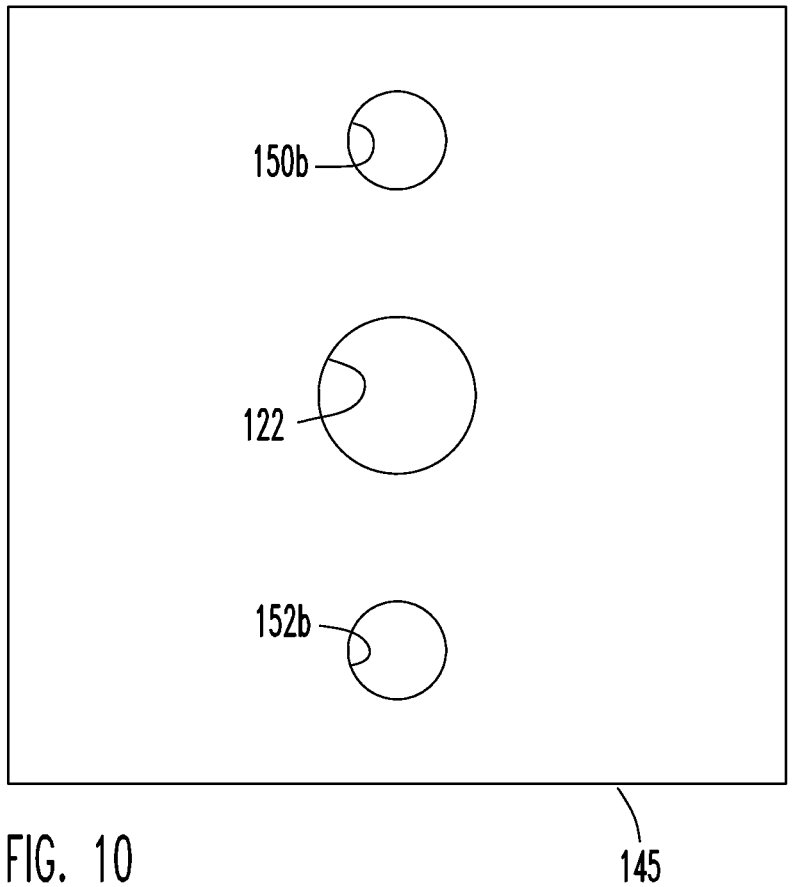
FIG. 10 is a top view of the upper intermediate component block of the extrusion die shown in FIG. 7 and taken along line 10-10 of FIG. 7.
Figure 11:
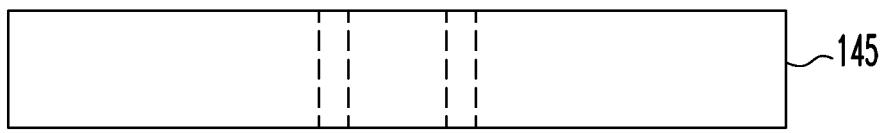
FIG. 11 is a side view of the upper intermediate component block.

FIG. 17 illustrates a portion of a second extrusion die 210. Extrusion die 210 is similar to the extrusion die 110 but the flow channel 212 flowing from the reservoir 214 to the discharge opening 216 flows parallel to the bottom die face 218.

Figure 18:
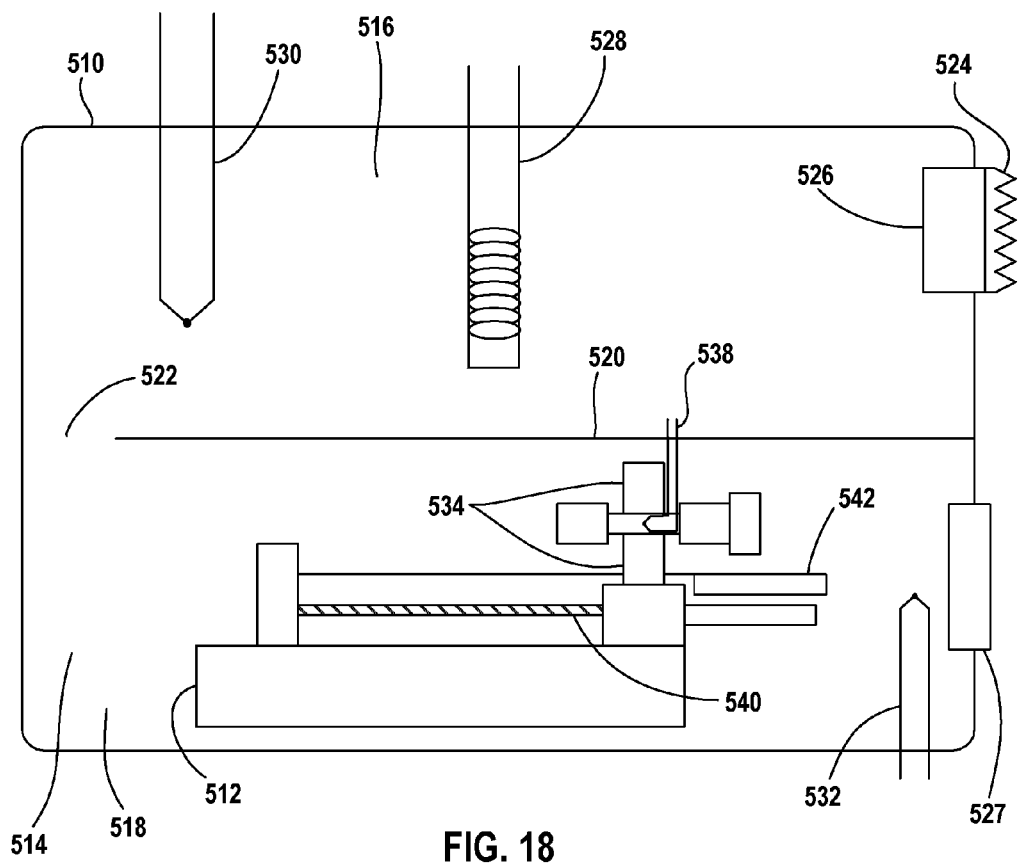
FIG. 18 is a schematic view of a second testing machine for flowing a grease sample, the testing machine within an environmental chamber.

FIG. 18 illustrates an environmental chamber 510 that houses a testing machine 512 similar to the testing machine 10. The environmental chamber 510 warms the grease being tested by the testing machine 512 as well as the other test components to a desired test temperature as will be described in more detail below.

Environmental chamber 510 has an interior chamber 514 divided into upper and lower chambers 516, 518 respectively by an interior horizontal wall 520. Wall 520 extends partway to the opposite side of the chamber, defining a flow channel 522 communicating the upper and lower chambers. Testing machine 512 is located in the lower chamber 518.

Air is drawn into the upper chamber 516 through an intake filter 524 by a muffin fan 526, and is exhausted out of the lower chamber 518 through an air outlet 527. A heating coil 528 upstream from the testing machine 512 heats the air flowing through the upper chamber to the desired test temperature. A control system (not shown) automatically regulates the output of the heating coil in response to air temperature and includes two thermocouples 530 and 532 located upstream and downstream from the test machine 512. The warmed air mixes in the upper chamber to provide a flow of uniformly heated air to the lower chamber.

Figure 19:
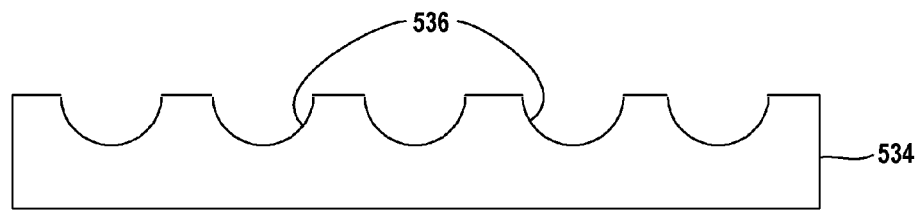
FIG. 19 is a side view of the yoke of the testing machine shown in FIG. 18.

Test machine 512 is designed to simultaneously hold and test a number of housings 12 that contain the grease samples to be tested. The housings 12 are held between a pair of like yokes 534, see FIG. 19. Each yoke 534 includes a number of notches 536 that cooperatively receive and hold the housings 12. The adjacent ends of the yokes are hingedly connected and enable the yokes to open or close to install or remove housing from between the yokes as needed.

The devices are held such that the force member 24 simultaneously drives the piston shafts 18 and extrudes grease from the grease-sampling devices at the same time. A separate load cell 22 is provided between each shaft 18 and the force member 24 to individually measure the force needed to extrude grease from each device.

In operation, air is drawn into the environmental chamber 510 and is heated until both thermocouples 530, 532 indicate the air flowing through the chamber has reached the desired test temperature. In the illustrated embodiment the test temperature is 40 degrees Centigrade, but a different test temperature can be used if desired.

The control circuit includes a timer (not shown) that delays actuation of the test machine 512 a predetermined delay period to assure that the grease in the sampling devices has also reached the test temperature. The delay period can be determined by placing instrumented grease-sampling devices in the test machine 512 (the instrumentation represented by thermocouple 538) and measuring the time needed for the grease to reach test temperature after the air flow has reached test temperature.

Once the delay period has passed, force member 24 is driven by screw-thread drive 540 to push the piston rods 18 and push grease to the extrusion dies attached to the housings 12. The extruded grease from the dies is deposited on a moving glass substrate 542 as previously described. The output data of the load cells 22 is recorded as a function of force member displacement, and a force curve is simultaneously generated for each grease sample.

While we have illustrated and described preferred embodiments, it is understood that this is capable of modification, and we therefore do not wish to be limited to the precise details set forth, but desire to avail ourselves of such changes and alterations as fall within the purview of the following claims.

The invention claimed is:

1. An extrusion die for extruding a uniform flow of new or used grease, the extrusion die comprising:
   an inlet opening to receive the grease, a discharge opening to discharge the extruded grease, and a flow channel fluidly connecting the inlet opening and the discharge opening to flow grease in a downstream direction through the flow channel from the inlet opening to the discharge opening, the discharge opening having a shape defining the cross-section shape of the grease extruded from the die; and
   a flow restriction in the flow channel, and a baffle in the flow restriction, the baffle extending at an acute angle with respect to the direction of flow through the flow restriction.

2. The extrusion die of claim 1 wherein the baffle is disposed at about a 30-degree angle with respect to the direction of flow through the flow restriction.

3. The extrusion die of claim 1 wherein the baffle extends along a longitudinal axis and has a "V"-shaped longitudinal cross-section.

4. The extrusion die of claim 1 wherein the flow restriction comprises a portion that extends in an upstream direction from the baffle.

5. The extrusion die of claim 1 wherein the flow channel has a maximum cross-sectional flow area, the extrusion die further comprising a chamber in the flow channel, the chamber having a cross-sectional flow area greater than the maximum cross sectional flow area of the flow channel.

6. The extrusion die of claim 5 wherein the flow restriction discharges into the chamber.

7. A method of measuring a characteristic property of grease by measuring the force needed to flow an amount of grease through a flow channel, the flow channel having an intake opening and a discharge opening, the discharge opening defining the cross-sectional area of the grease discharged from the flow channel, the method comprising the steps of:
   (a) pushing a constant volumetric flow of grease into the inlet opening and flowing grease through the flow channel under the impetus of the grease being pushed into the opening; and
   (b) measuring the force needed to maintain the constant volumetric flow of grease into the flow channel as a function of time while grease is being discharged from the discharge opening.

8. The method of claim 7 comprising the step of:
   (c) flowing the grease through a flow restriction forming part of the flow channel, the flow restriction having a smaller flow area than the inlet opening.

9. The method of claim 8 wherein the flow restriction comprises a first portion and a second portion, the grease flowing in a first direction in the first flow restriction portion and flowing in an opposite second direction in the second flow restriction portion.

10. The method of claim 9 wherein the first and second flow restriction portions are joined by a portion of the flow channel having a flow area larger than the flow areas of either flow restriction portions.

11. The method of claim 8 wherein the flow restriction has a smaller flow area than the discharge opening.

12. The method of claim 7 comprising the step of:
   (c) flowing the grease in the flow channel past a baffle, the baffle disposed at an oblique angle in the flow channel.

13. The method of claim 7 wherein the flow channel comprises a reservoir having an intake end and a discharge end, and the flow areas of the flow channel adjacent both ends of the reservoir has a smaller flow area than the flow area of the reservoir.

14. The method of claim 13 wherein the flow area of the flow channel from the reservoir to the discharge end is a constant flow area.

15. The method of claim 13 comprising a weir at the downstream end of the reservoir.

* * * * *